United States Patent
Troxler

(10) Patent No.: US 10,415,205 B2
(45) Date of Patent: *Sep. 17, 2019

(54) PAVING RELATED MEASURING DEVICE INCORPORATING A COMPUTER DEVICE AND COMMUNICATION ELEMENT THEREBETWEEN AND ASSOCIATED METHOD

(71) Applicant: Troxler Electronic Laboratories, Inc., Research Triangle Park, NC (US)

(72) Inventor: Robert Ernest Troxler, Raleigh, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/603,387

(22) Filed: May 23, 2017

(65) Prior Publication Data

US 2017/0321387 A1    Nov. 9, 2017

Related U.S. Application Data

(63) Continuation of application No. 14/164,290, filed on Jan. 27, 2014, now Pat. No. 9,657,446, which is a continuation of application No. 13/367,018, filed on Feb. 6, 2012, now Pat. No. 8,682,605, which is a continuation of application No. 12/123,242, filed on May 19, 2008, now Pat. No. 8,112,242, which is a continuation of application No. 10/817,169, filed on Apr. 2, 2004, now Pat. No. 7,376,530, which is a continuation-in-part of application No. 10/269,843, filed on Oct. 11, 2002, now Pat. No. 6,915,216.

(51) Int. Cl.
| | |
|---|---|
| *E02D 1/02* | (2006.01) |
| *G06F 3/048* | (2013.01) |
| *E01C 19/00* | (2006.01) |
| *E02D 1/00* | (2006.01) |
| *G01N 9/00* | (2006.01) |

(52) U.S. Cl.
CPC .............. *E02D 1/025* (2013.01); *E01C 19/00* (2013.01); *E02D 1/00* (2013.01); *E02D 1/022* (2013.01); *G01N 9/00* (2013.01); *G06F 3/048* (2013.01); *C08L 2555/10* (2013.01)

(58) Field of Classification Search
CPC ....... C08L 2555/10; E01C 19/00; E02D 1/00; E02D 1/022; E02D 1/025; G01N 9/00; G06F 3/048
USPC ......... 702/33, 127, 134, 137, 150, 159, 166, 702/171, 172, 189, 107; 250/252.1, 253; 340/539.13; 73/32, 78, 146
See application file for complete search history.

(56) References Cited

U.S. PATENT DOCUMENTS

| | | | |
|---|---|---|---|
| 5,923,726 A * | 7/1999 | Regimand | G01N 23/06 250/252.1 |
| 6,915,216 B2 | 7/2005 | Troxler et al. | |
| 6,995,667 B2 * | 2/2006 | He | G01S 5/02 340/539.13 |

(Continued)

*Primary Examiner* — John H Le
(74) *Attorney, Agent, or Firm* — NK Patent Law

(57) ABSTRACT

A system configured to determine a property of a paving-related material is provided. The system includes a measuring device configured for measuring a property of a paving-related material and a cellular computer device configured for being in communication with and receiving data from the measuring device.

8 Claims, 7 Drawing Sheets

(56) References Cited

U.S. PATENT DOCUMENTS

| | | |
|---|---|---|
| 7,376,530 B2 | 5/2008 | Bienvenu et al. |
| 8,112,242 B2 | 2/2012 | Troxler |
| 8,682,605 B2 | 3/2014 | Troxler |
| 9,657,446 B2 | 5/2017 | Troxler |

\* cited by examiner

PAVING RELATED MEASURING DEVICE INCORPORATING A COMPUTER DEVICE AND COMMUNICATION ELEMENT THEREBETWEEN AND ASSOCIATED METHOD

CROSS-REFERENCE TO RELATED APPLICATIONS

The application is a continuation of U.S. patent application Ser. No. 14/164,290 filed on Jan. 27, 2014, which is a continuation of U.S. patent application Ser. No. 13/367,018, filed on Feb. 6, 2012, now U.S. Pat. No. 8,682,605, which is a continuation of U.S. patent application Ser. No. 12/123,242, filed on May 19, 2008, now U.S. Pat. No. 8,112,242, which is a continuation of U.S. patent application Ser. No. 10/817,169, filed on Apr. 2, 2004, now U.S. Pat. No. 7,367,530, which is a continuation-in-part of U.S. patent application Ser. No. 10/269,843, filed on Oct. 11, 2002, now U.S. Pat. No. 6,915,216, all of which are hereby incorporated by reference in their entirety.

FIELD OF THE INVENTION

The present invention relates to measurement devices for measuring properties of aggregates, soils, and paving materials and, more particularly, to a system and method for determining a property of a paving-related material sample with a measuring device in communication with a computer device via a communication element.

DESCRIPTION OF RELATED ART

The process of paving roadways is subject to standards which direct the necessary characteristics of the paving used to form the roadway. As such, actual data from the paving contractor supporting such compliance with the applicable standards is often a mandatory requirement of the entity owning the roadway. Often, the entity is part of the government such as, for example, the Department of Transportation of the state. In order to determine compliance with these various standards, the contractor must often perform certain measurements in the field with certain measuring devices at certain points as the roadway is being paved. However, such measuring devices used in the field often use bulky and cumbersome keypads and/or older technology displays having limited capabilities with respect to collecting, storing, manipulating, and displaying the necessary data. In other instances, the keypad and display are integrated into the measuring device itself, wherein the measuring device most be programmed with the measurement parameters, via the keypad, prior to or concurrently with performing the property measurement. However, the measuring device is typically required to be placed in contact with the roadway to initiate the property measurement. Once the measurement is completed, the measured value must then be read by the operator. Thus, in both the measurement preparation step and the measurement reading step, the entire device Is usually required to be placed on a raised surface or the operator must stoop to the level of the measuring device on the roadway, both of which may cumbersome, inconvenient, uncomfortable, or otherwise undesirable.

In some instances, the measuring device may require the contractor to manually gather the necessary data and/or keep any notes using paper and a writing utensil. The contractor not only must gather the data from the site, hut must also transcribe or otherwise manipulate the collected data such that the data can be presented to the owning entity in a usable and/or the required format. The described data collection process, though, is prone to inaccuracies, both in the collection of the data and the transcription and/or manipulation of the data. Such a process may also, in some instances, become more complicated if there is uncertainty between the contractor and the owning entity regarding a measurement and/or the location of that measurement. Accordingly, this may lead to disputes since the owning entity is often not present to actually witness the applicable measurements that are generally manually performed by the contractor. Further, the owning entity usually receives a manually prepared record of the time, date, location, and value of each measurement as evidence of the contractors compliance with the applicable standards.

Thus, there exists a need for a system capable of determining a desired property of a sample of a paving-related material, wherein such a system is further capable of associating other measurements or data, such as location, with the determined property of the sample, so as to provide data having the content and format required by the owning entity, while also providing the owning entity with some assurances of accuracy and reliability of the data. There also exists a need for such a system that is more user-friendly and more flexible with respect to determining the capabilities of the measuring device. Such a system should also overcome the requirement that the measuring device be placed on a raised surface or the operator stoop to the level of the device on the roadway in order to program and/or read the device.

BRIEF SUMMARY OF THE INVENTION

The above and other needs are met by the present invention which, in one embodiment, provides a system adapted to determine a property of a paving-related material Such a system comprises a measuring device for selectively and directly measuring the property of the paving-related material. A computer device is capable of executing a software program product and communicating with the measuring device. The computer device is configured to direct the measuring device to measure the property of the paving-related material according to a parameter determined by the software program product, and to receive data comprising the measured property of the paving-related material from the measuring device. A communication element is operably engaged between the measuring device and the computer device so as to allow communication therebetween. The communication element is configured to allow the computer device to be spaced apart from the measuring device, thereby allowing tire computer device to be prepared, to include the parameter and to manipulate the data, in spaced apart relation with respect to the measuring device.

Still another advantageous aspect of the present invention comprises a method of determining a property of a paving-related material. First, a computer device is prepared to execute a software program product for directing a measuring device to directly measure the property of the paving-related material, according to a parameter determined by the software program product, and to receive data comprising the measured property of the paving-related material from the measuring device. The software program product is then executed. The executed software program product is communicated from the computer device to the measuring device via a communication element operably engaged therebetween. The communication element is configured to allow the computer device to be spaced apart from the measuring device such that the computer device can be prepared, in spaced apart relation with respect to the measuring device, to include the parameter and to manipulate the data.

Yet another advantageous aspect of the present invention comprises a system adapted to cooperate with a measuring device to selectively and directly measure a property of a paving-related material. Such a system includes a computer device capable of executing a software program product and communicating with the measuring device. The computer device is configured to direct the measuring device to measure the property of the paving-related material according to a parameter determined by the software program product, and to receive data comprising the measured property of the paving-related material from the measuring device. A communication element is operably engaged between the measuring device and the computer device so as to allow communication therebetween. The communication element is configured to allow the computer device to be spaced apart from the measuring device, thereby allowing the computer device to be prepared, to include the parameter and to manipulate the data, in spaced apart relation with respect to the measuring device.

Thus, embodiments of the present invention meet the above-identified needs and provide distinct advantages as further detailed herein.

BRIEF DESCRIPTION OF THE SEVERAL
VIEWS OF THE DRAWING(S)

Having thus described the invention in general terms, reference will now be made to the accompanying drawing, which is not necessarily drawn to scale, and wherein:

DETAILED DESCRIPTION OF THE
INVENTION

The present inventions now will be described more fatty hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
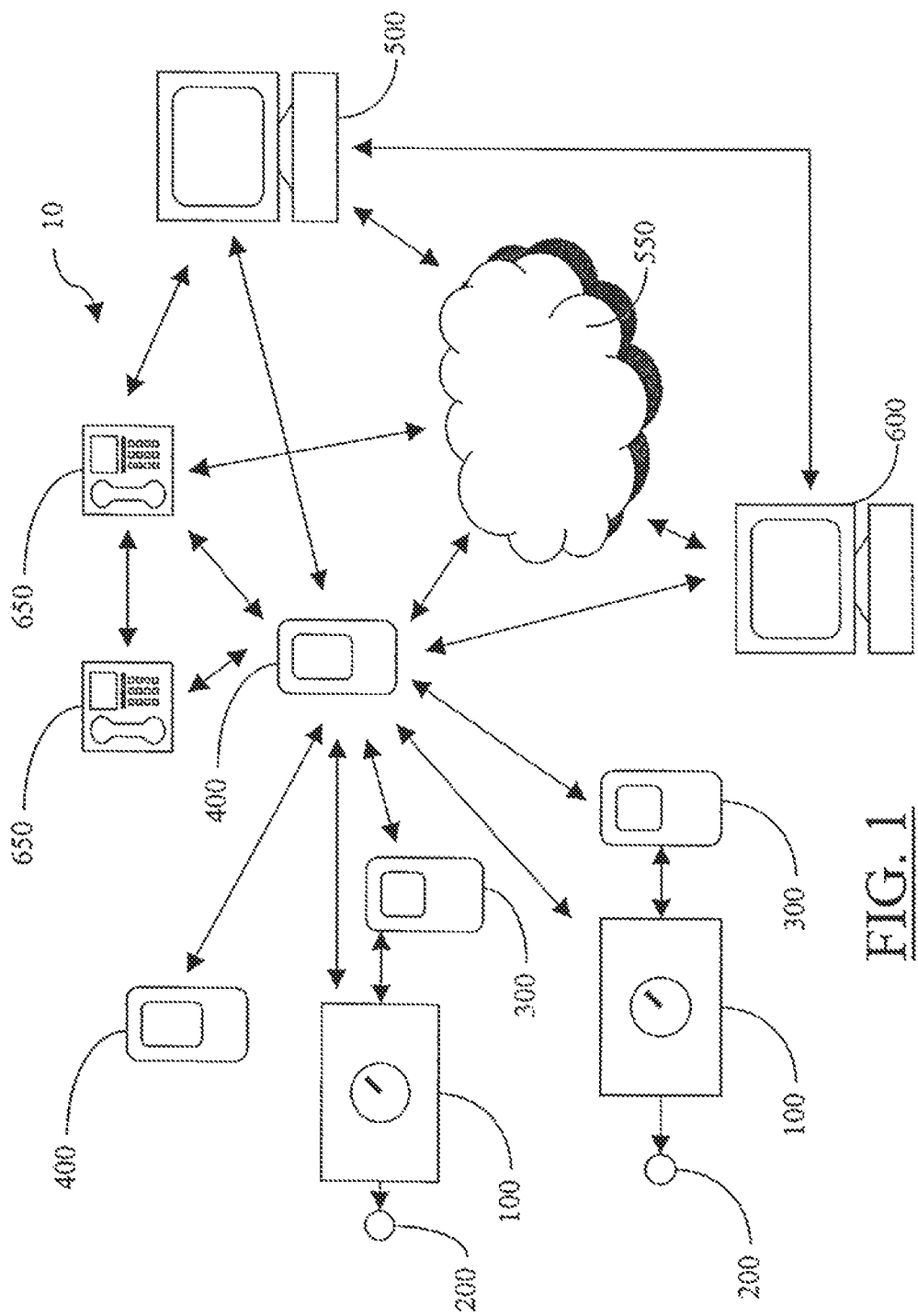
FIG. 1 is a schematic illustration of a system for determining a property of a paving-related material, sample with a measurement device having a locating device operably engaged therewith, the measuring device and the locating device being in communication with a computer device, according to one embodiment of the present invention.
Figure 2:
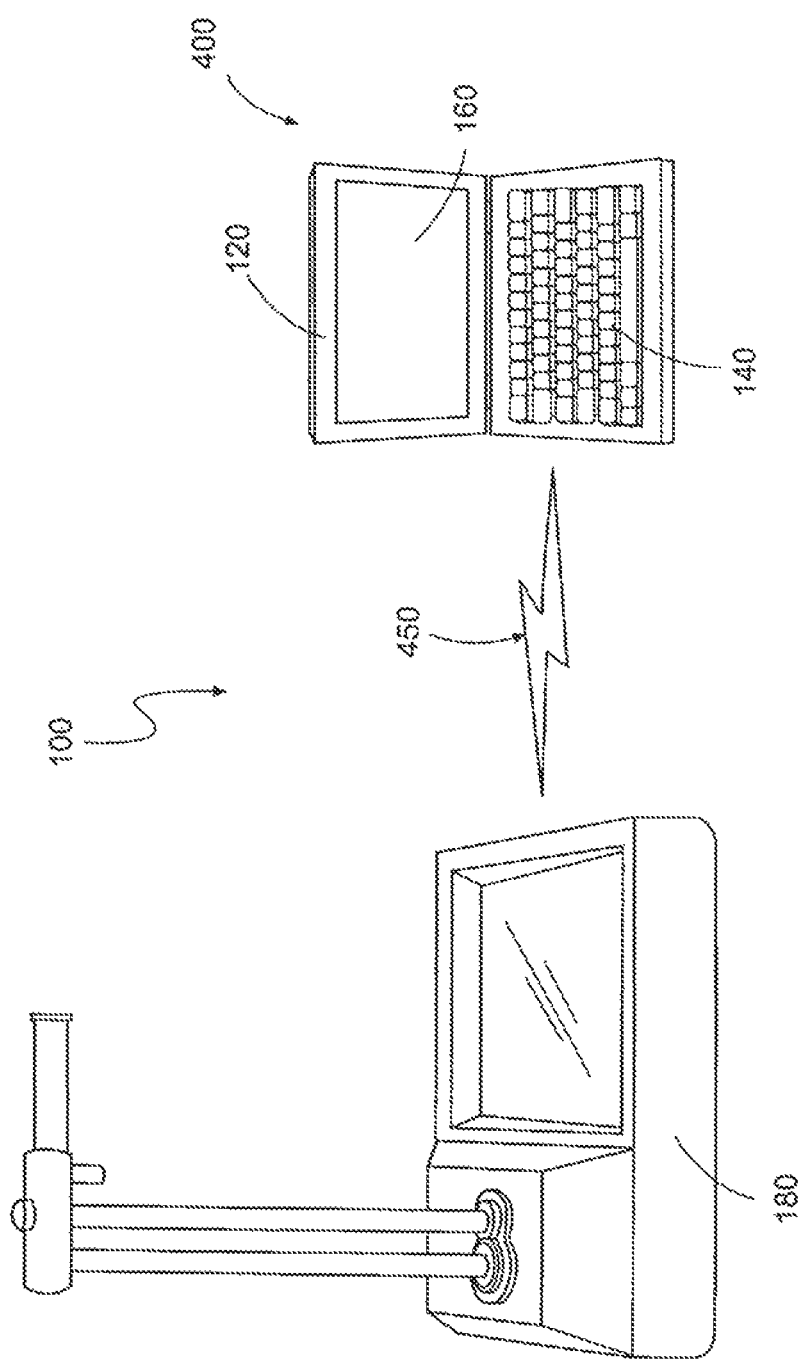
FIG. 2 is a schematic illustration of a measurement device in communication with a computer device via a wireless connection, according to one embodiment of the present invention.

FIG. 1 illustrates a system for determining a property of a paving-related material according to one embodiment of the present invention, the system being indicated generally by the numeral 10. Such a system 10 comprises at least measuring device 100 for measuring a property of a sample 200 of a paving-related material such as, for example, an asphalt paving mix, a soil, or an aggregate. For example, one measuring device 100 may comprise a nuclear density gauge such as, for instance, a Model 3451 Nuclear Density Gauge manufactured by Troxler Electronic Laboratories, for determining the density of the sample 200, while another measuring device 100 may comprise, for instance, a moisture meter such as, for example, a Model 4300 Moisture Meter manufactured by Troxler Electronic Laboratories, for determining the moisture content of the sample 200. Other possibly suitable measuring devices 100 include, for example, any other instrumentation capable of determining density such as a Seismic Pavement Analyzer (SPA), a portable SPA (PSPA) manufactured by Geomedia, a Model H-4140 stiffness gauge distributed by Humboldt Manufacturing, a Model 8000 Falling Weight Deflectometer (FWD) manufactured by Dynatest, and/or various electromagnetic and/or microwave devices such as a ground penetrating radar (GPR) type asphalt instrument from Geophysical Survey Systems or Infrasense, or various RF devices such as the Pave Tracker and the PQI from Trans-Tech, One skilled in the art will also appreciate that many other particular measuring devices 100 may also be used herein and selected from any number of devices such as a nuclear density gauge, a nuclear moisture gauge, a seismic pavement analyzer, a stiffness gauge, a falling weight deflectometer, a ground penetrating radar device, a radio frequency device, an electromagnetic device, a microwave device, a surface roughness measuring device, a pavement temperature sensor, a pavement temperature measuring device, and combinations thereof. Such measuring devices 100 are, in some instances, generally directed to measuring density-related parameters such as, for example, a modulus of elasticity (shear and Young's), a stiffness of the soil or asphalt sample, a void content, and hulk density, wherein the determination of such density-related parameters will be readily appreciated by one skilled in the art. Further, as will be appreciated by one skilled in the art, the measuring device 100 may comprise any other appropriate field or laboratory device, or combinations thereof, capable of performing the desired property measurements of such paving-related materials.

In some of the aforementioned measuring devices 100 and as further shown in FIGS. 2-5, the control system 120 therefor comprising, for example, a keypad 140 and a display 160, may be integrated with or securely attached to the property measuring portion 180 of the measuring device 100. That is, the measuring portion 180 of the measuring device 100 and the control system 120 may be built into a single case or enclosure so as to provide a self-contained device. However, such as integrated measuring device 100 may be cumbersome or inconvenient for the operator, particularly in instances where the measuring device 100 must be put into contact with the pavement in order to perform the property measurement. Thus, in order to program the control system 120 or read the measurement from the display 160, the operator often must place the measuring device 100 onto a raised platform or the operator must stoop down to the level of the measuring device 100 on the pavement. In either of these instances, operation of the measuring device 100 may be cumbersome or inconvenient. The system 10 thus further includes a computer device 400 such as, for example, a Personal Digital Assistant (PDA), custom configured controller, other appropriate computer device, such as a "smart device" or the like configured to be in communication with the measuring device 100 via a communication element 450. The computer device 400 may be provided in addition to the control system 120 or in the alternative to the control system 120. Though the system 10 is described herein in terms of the computer device 400 being provided as an alternative to the control system 120, one skilled in the art will appreciate that there may be many ways of incorporating the computer device 400 in addition to the control system 120 such that one or the other, or both, may be used to control, direct, or otherwise determine the parameters used by the measuring device 100 to obtain the necessary measurements and provide the corresponding data. Some embodiments of the invention may thus provide a computer device 400 and/or communication element 450, as described further herein, that may be used with many different measuring devices 100, examples of which are presented herein, or combinations of such measuring devices 100, and are not associated with any particular measuring device 100.

Figure 3:
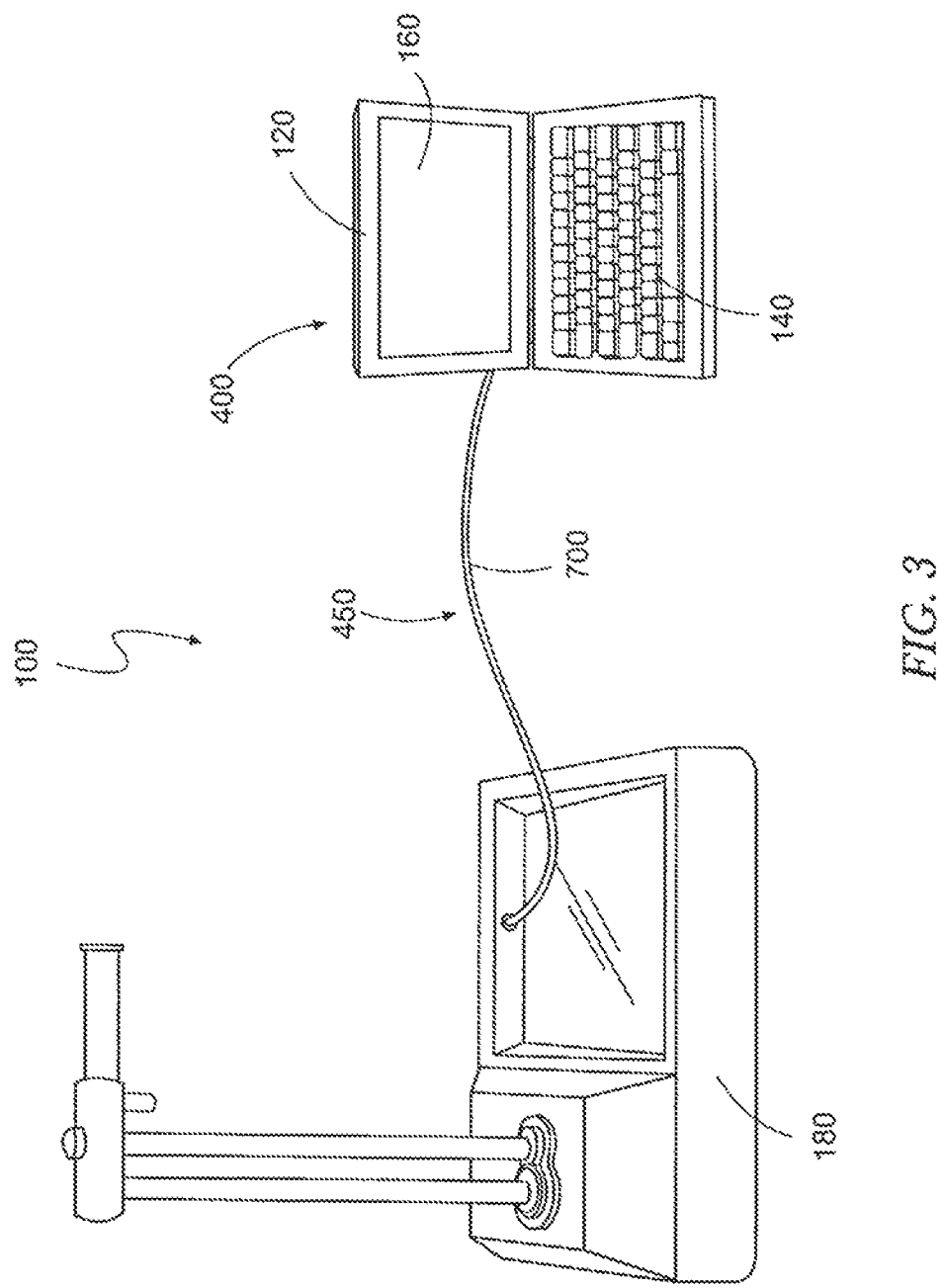
FIG. 3 is a schematic illustration of a measurement device in communication with a computer device via a hardwire connection, according to one embodiment of the present invention.

The communication element 450 operably engaged between the computer device 400 and the measuring device 100 may be configured in many different manners. For example, the computer device 400 may be configured to communicate with the measuring device 100, a locating device 300 as discussed further herein, or other computer devices 400 using, for example, a communication element 450 configured to use Bluetooth™ wireless technology using appropriate wireless transceivers operable engaged with the appropriate component, as shown schematically in FIG. 2. However, the wireless communication element 450 may implement many other analog and/or digital wireless communication systems and/or modulation schemes such as, for example, IR, FSK, PSK, or radio frequency systems, as will be appreciated by one skilled in the art. According to other embodiments of the present invention, the communication element 450 may comprise a wire element 700 connected between the measuring device 100 and the computer device 400, as shown in FIG. 3. In such instances, the wire element 700 is configured to be extendable such that the computer device 400 can be physically separated from the measuring device 100, but remain in communication therewith via the wire element 700. Further, the wire element 700 may be configured to example, in a flexible cord form, in a coil form, or in a flexible cord form engaged with an auto-retraction device. Thus, in instances where the communication element 450 is embodied in wireless communication technology or comprises a wire element 700, communication between the computer device 400 and the measuring device 100 may be selectively established at any time. That is, such communication may be established in preparing or programming the computer device 400 in order to, for example, determine one or more parameters affecting the property measurement performed by the measuring device 100. Communication may also be established to, for instance, monitor the progress of measurements, adjust one or more-parameters during a measurement process, or to receive measurement data from the measuring device 100.

Figure 4A:
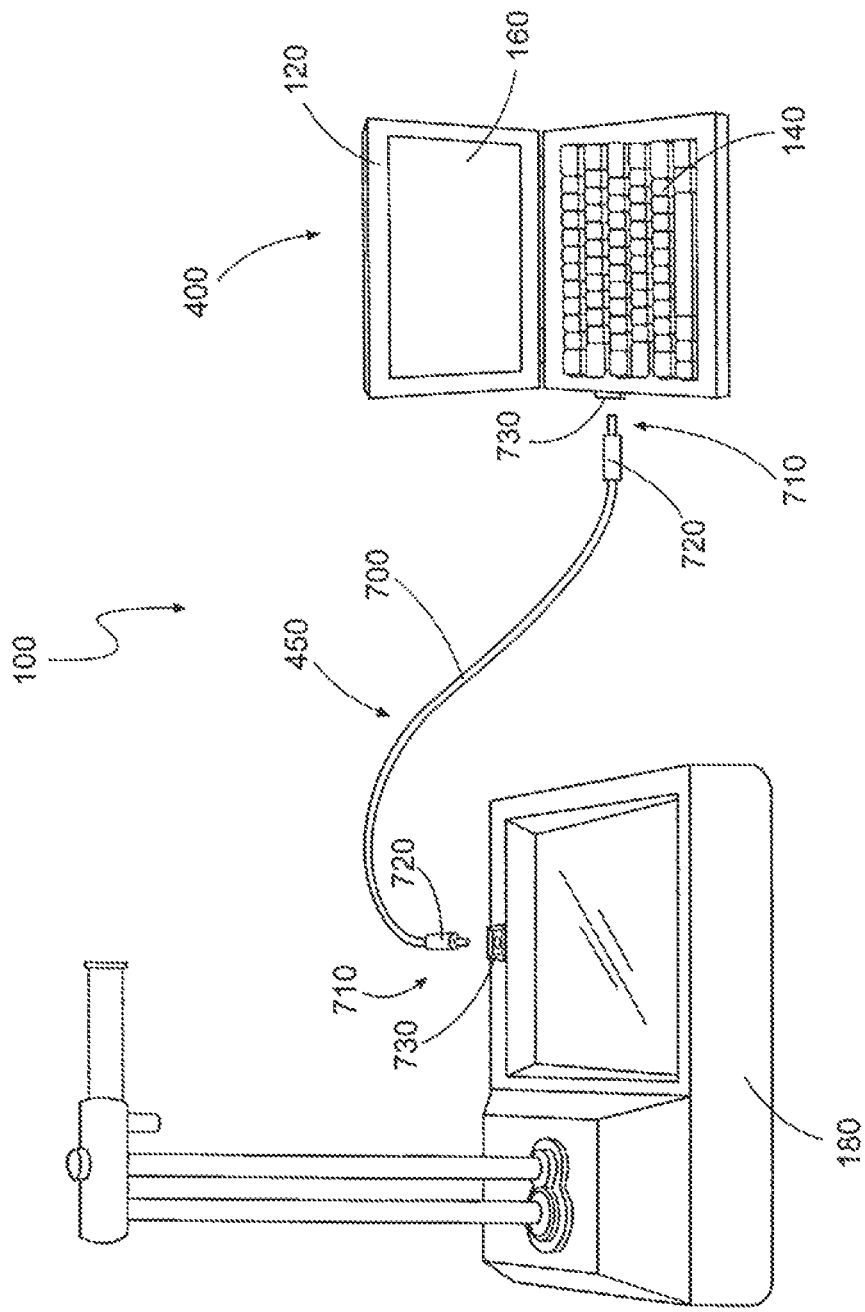
FIGS. 4A-4C are schematic illustrations of a measurement device in communication with a computer device via a wire having a connector at either or both ends, according to one embodiment of the present invention.
Figure 4B:
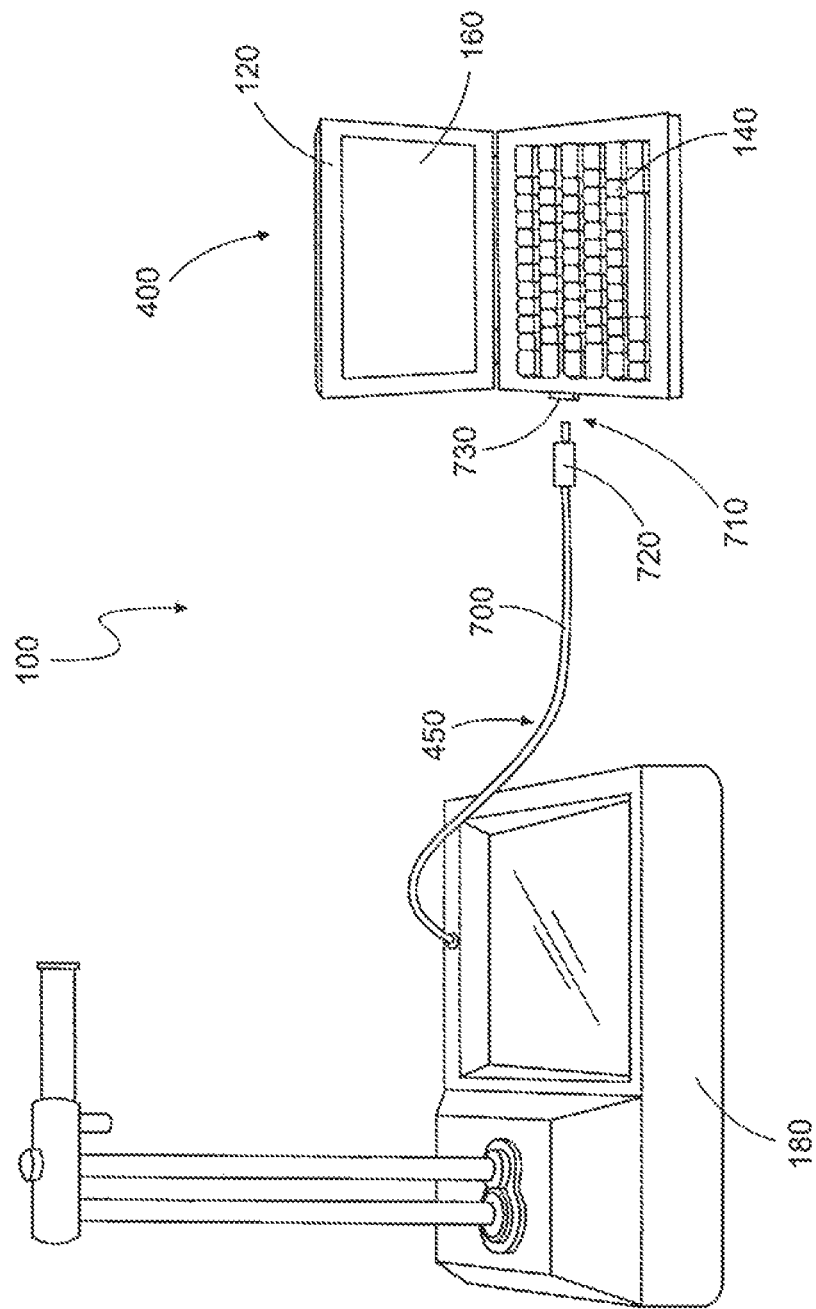
Figure 4C:
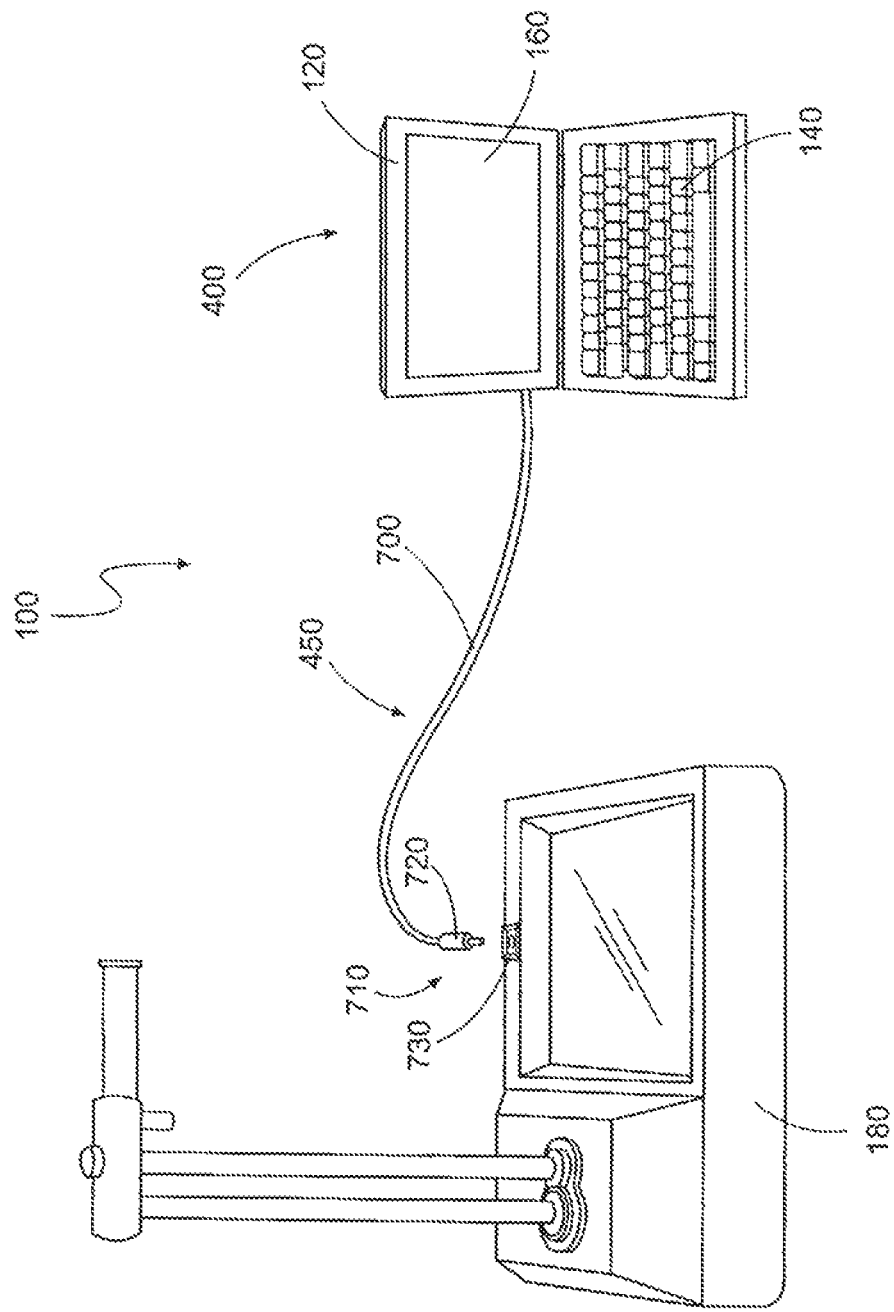
Figure 5:
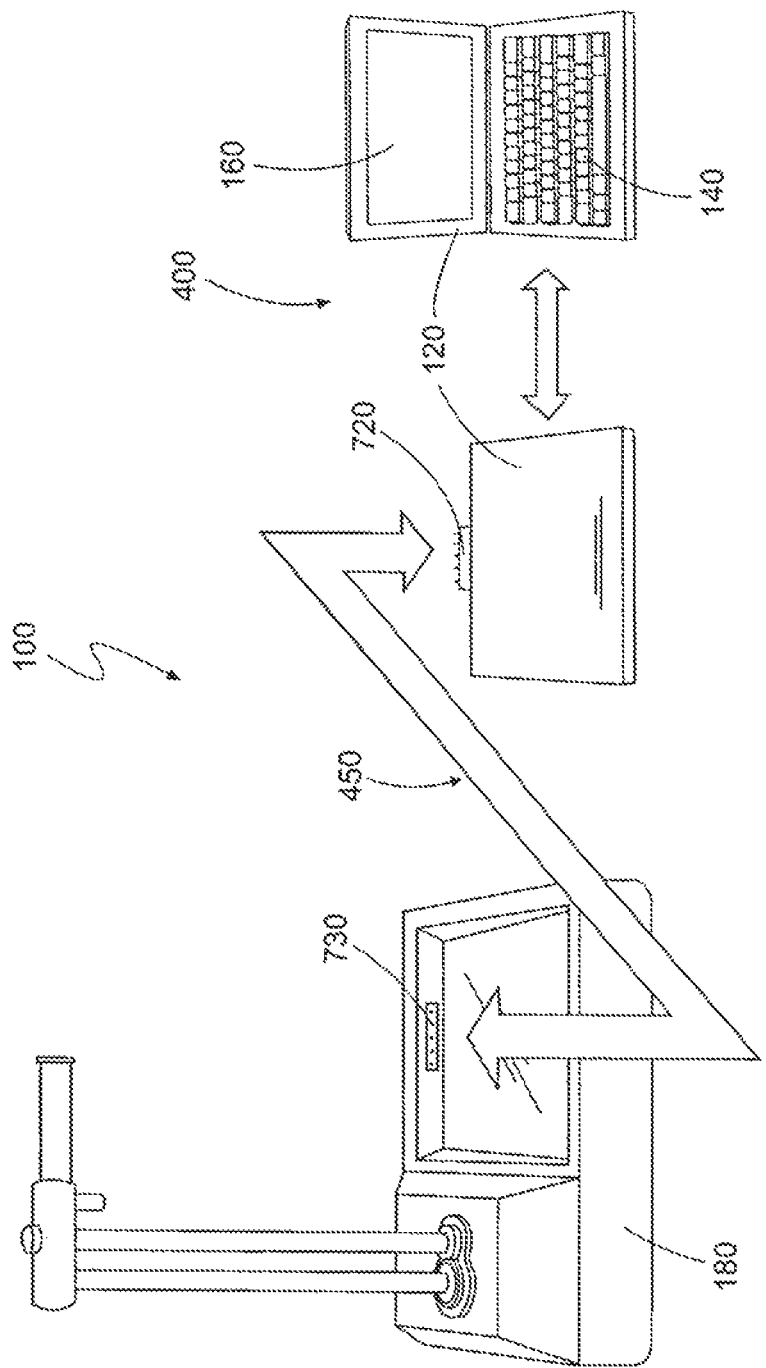
FIG. 5 is a schematic illustration of a measurement device in communication with a computer device via a connector, according to one embodiment of the present invention.

In other embodiments, as shown, in FIGS. 4A-4C and 5, the system 10 may include a connector 710 comprising a first connector portion 720 and a corresponding second connector portion 730 disposed between the computer device 400 and the measuring device 100. The connector portions 720, 730 are configured to be removably engageable and, when engaged, allow communication between the computer device 400 and the measuring device 100. In some instances, the connector 710 may be disposed directly between the computer device 400 and the measuring device 100. That is, the first connector portion 720 may be engaged with the computer device 400 while the second connector portion 730 is engaged with the measuring device 100. In such a configuration, the computer device 400 may engage the measuring device 100 in a "docking station" form as shown in FIG. 5, where the computer device 400 can be installed in a corresponding receptacle defined by the measuring device 100 such that the connector portions 720, 730 engage and allow communication between the computer device 400 and the measuring device 100.

In other instances, the connector 710 may be established between the wire element 700 and the computer device 400 and/or between the wire element 700 and the measuring device 100. That is, the wire element 700 may be engaged with either the computer device 400 or the measuring device 100 at one end, while the other end of the wire element 700 is engaged with the first connector portion 720. Such configurations are schematically illustrated in FIGS. 4B and 4C. In such instances, the computer device 400 or the measuring device 100, whichever is not engaged with the wire element 700, is provided with the second connector portion 730. In some instances, however, the wire element 700 may include a connector 710 at both ends such that the wire element 700 can be removed from either or both of the computer device 400 and the measuring device 100, as shown in FIG. 4A. One skilled in the art, though, will appreciate that the connector 710, if used, can be implemented at any position along the length of the wire element 700. Thus, in embodiments employing such a connector 710, the computer device 400 may be physically separated from and removed from communication with the measuring device 100. That is, the computer device 400 can be prepared or programmed to, for example, determine one or more parameters affecting the property measurement performed by the measuring device 100, monitor the progress of measurements, adjust one or more parameters during a measurement process, or to receive measurement data from the measuring device 100, while separated from and not in communication with the measuring device 100. Once the preparation process is completed, the computer device 400 may be reconnected to the measuring device 100 via the connector(s) 710 and, in some instances, via the wire element 700, before the software run by the computer device 400 is executed and the measuring device 100 is directed to perform the selected property measurement(s) and/or handle the measurement data determined by the measuring device 100.

With the computer device 400 being configured to be physically separable from the measuring device 100, several advantages may be realized. For example, the operator is not required to be on the same level as the measuring device 100 in order to prepare or otherwise program the computer device 400. That is, the measuring device 100 can be placed on the pavement in a designated position, for the desired property measurement, while the computer device 400 may be physically separated from the measuring device 100 such that the operator can prepare or program the computer device at a separate raised location. In this manner, the measuring device 100 is not required to be moved to the same raised location, as the computer device 400 and the operator does not have to stoop to the level of the measuring device 100 on the pavement in order to prepare or program the computer device 400. The same advantages may be realized where the operator has to read the measurement data determined by the measuring device 100. Where a connector 710 is implemented, the computer device 400 may be taken out of communication with the measuring device 100 and handled separately therefrom. If, for example, the computer device 400 requires upgrade or service, the measuring device 100 does not also have to be transported to a service center along with the computer device 400. In some instances, the measuring device 100 may also be directed to perform the property measurement while the computer device 400 is physically separate therefrom, but in communication therewith, so as to provide remote control tor the measuring device 100 and to allow the measurement data to be remotely read and processed by the computer device 400.

The separable computer device 400 may provide even more advantages. For instance, the measuring device 100 itself may be capable of performing a plurality of functions. Each function may, for instance, be related to a particular parameter used by the measuring device 100 to measure a particular property of the sample 200 and/or the type of property measurement returned by the measuring device 100 and/or the handling, manipulation, or direction of that data. The functional, capabilities of the measuring device 100, however, are generally determined by the software executed by the computer device 400. That is, the software executed by the computer device 400 is communicated to the measuring device 100 and thereby directs the measuring device 100 to perform a function involving a particular parameter and to handle the measurement data in a particular manner. Accordingly, in some instances, the software may be configured so as to provide the computer device 400 with the capability of directing the measuring device 100 to perform only a certain combination of functions out of the plurality of functions of which the measuring device 100 is capable. In practical terms, such a capability may allow, for example, various models to be provided using the same measuring device 100 and computer device 400, but by providing various levels of software. That is, a base level model may include software capable of directing the measuring device 100 to perform a certain amount or combination of functions. A higher level model may include the same measuring device 100 and computer device 400, but may include software capable of directing the measuring device 100 to perform an increased number or different combinations of functions over the base model. In such instances, the software may be written in the same computer language over the model range and, if the customer or end user eventually requires the capabilities of a higher model, such as upgrade may be provided to the customer or end user with a software upgrade. That is, additional functional capabilities or a different combination of functions may be provided by updating the software executed by the computer device 400. Such a software upgrade may be supplied on a storage media shipped to the customer or may be accomplished, for example, as a download from the Internet or other central computer device 500 or as a flash upgrade to the computer device 400.

In particularly advantageous embodiments, each measuring device 100 may further include a locating device 300 operably engaged therewith, wherein such a locating device 300 may comprise, for example, a Global Positioning System (GPS) device or other satellite and/or land-based beacon type of locating device implementing, in some instances, a location enhancement scheme such as Differential GPS (DGPS) or a Wide Area Augmentation Scheme (WAAS). However, many different forms of locating devices and/or location, enhancement schemes will be appreciated by one skilled in the art as being within the spirit and scope of the present invention. The locating device 300 is configured to determine the position/location of the respective measuring device 100, wherein, in one embodiment, the locating device 300 is configured to determine the position/location in latitude, longitude, and/or altitude coordinates, though any other suitable coordinate system may be used. Since the locating device 300 is operably engaged, with the measuring device 100, in addition, to the purposes as described herein, the locating device 300 may also be useful in, for example, locating and recovering lost or stolen, measuring devices 100 as will be appreciated by one skilled in the art. For example, a measuring device 100/locating device 300 unit may be configured to be in communication with a beacon device (not shown), wherein the beacon device may be further configured to transmit a signal to the measuring device 100/locating device 300 unit if it is determined that the unit is lost, misplaced, or stolen. The unit, in response to the signal, may then be configured to send a signal back to the beacon device indicative of the physical position and/or movement parameters of the unit, as determined by the locating device 300. In other instances, the unit may be configured to send a signal to the beacon device indicative of the physical position and/or movement parameters of the unit if the unit becomes separated from the beacon device by more than a selected distance. In this regard, the computer device 400 may also be operably engaged, or communicable with the locating device 300 operably engaged with the measuring device 100 or, in other instances, the computer device 400 may have a separate locating device 300 operably engaged therewith.

In instances where the computer device 400 is configured to be in wireless communication with the measuring device 100, the computer device 400 may be configured to communicate with only a single measuring device 100/locating device 300 unit, with multiple measuring device 100/locating device 300 units, and/or with other computer devices 400 configured for a separate set of measuring device 100/locating device 300 units. In such instances, the computer device 400 and/or the measuring device 100/locating device 300 units can be configured with appropriate electronic coded keys, such as an RFID tag, or other identifiers so as to ensure that a computer device 400 communicates only with the appropriate measuring device 100/locating device 300 units (and/or other computer devices 400), as will also be appreciated by one skilled in the art. For example, an identifier may comprise a digital key for coding a particular measuring device 100/locating device 300 unit with a computer device 400. Such identifiers may serve other purposes such as, for example, maintaining an inventory of measuring device 100/locating device 300 units or tracking such units in the field.

According to other advantageous aspects of the present invention, the computer device 400 is configured, to collect data from the measuring device 100/locating device 300/unit(s), sometimes in real time, wherein such data includes the measured sample property and the location of the measuring device 100 when the sample property is measured thereby. However, the computer device 400 may also be configured to be capable of performing many other tasks in addition to merely collecting the data from the measuring device 100/locating device 300 unit(s). For example, the computer device 400 may be configured to associate, for instance, a time and date stamp, or an electronic identifier for the measuring device 100 (type and/or serial number), the operator thereof, the sample 200, the locating device 300, the computer device 400 receiving the data, the operator thereof, and/or the contractor, with each sample property/measuring device location measurement performed by a measuring device 100/locating device 300 unit and transmitted to the computer device 400. In other instances, the computer device 400 may perform any or all necessary calculations and/or manipulate the data for display to a user, wherein, for example, the raw data could be displayed or the data may be manipulated to produce a variety of graphs and graphics that could then be presented to the user on a screen of the computer device 400. One skilled in the art will appreciate, however, that a wide variety of other functionality may also be implemented in the computer device 400. For example, the handheld computer device 400 may also be configured to have digital filtering or other digital signal processing incorporated therewith, or may be configured with many different capabilities for further enhancing the system 10.

According to further advantageous aspects of the present invention, each computer device 400 is configured to communicate the collected data with a central computer system 500, wherein the central computer system 500 may comprise, for example, a host system associated with the contractor. The central computer system 500 is further configured, in some embodiments, to house a database such as, for example, a geographic information system (GIS). One advantage of such a configuration is that the data may be collected at a central repository having a more expansive, secure, reliable, and stable data storage configuration than the computer device 400 which may have limited memory and which is subject to a relatively hostile environment in the field. The data may be collected from the computer device 400, for example, in real time (as each data element is collected), at the conclusion of a planned series of measurements, at the end of a day, at the end of a job, or on an otherwise periodic basis. The central computer system 500 may also have greater computing and analysis capabilities, as well as more extensive data presentation capabilities, for manipulating the collected data, wherein data from many different computer devices 400 may be collected for comprehensive analysis.

Each computer device 400 may communicate with the central computer system 500 by wireline or by many different wireless systems 550, as will be appreciated by one skilled in the art. For example, the communication may be accomplished via a wide area network (WAN), a local area network (LAN), a satellite network, or otherwise over the Internet. Voice/data network protocols and frequencies that may be supported include, but are not limited to, for example, the global system for mobile communications (GSM)/general packet radio service (GPRS), dual-mode advanced mobile phone service (AMPS)/circuit switched data and code division multiple access (CDMA/1×RTT) (used, for example, in U.S. PCS cellular telephone systems), TDMA, DataTAC, and Mobitex. Other network protocols and frequencies are known in the art and can be supported as well. For example, emerging technologies such, as 3G or the IEEE 802.11 protocol may be implemented or direct communication through Bluetooth™ technology may also be used. Further, even a conventional telephone system (POTS) may be implemented. As such, the data may be communicated in many different formats consistent with the many different communications options available, wherein the data may be, for example, included in a simple e-mail message, posted on a web page, or supplied in a complex encrypted data stream.

In one embodiment, the GPRS or CDMA wireless wide area network interface allows communication between the computer device 400 and public digital cellular telephone networks. As such, the computer device 400 may be, in some instances, configured as or may include a cellular telephone capable of allowing the user to communicate with other cellular telephones 650 over the public digital cellular telephone networks. Further, with such various communication options available, software updates and/or relevant data for the computer device 400, the measuring device 100, and/or the locating device 300 may be readily provided thereto by the central computer system 500 or any other authorized computer system associated with, for instance, the manufacturer of the particular component. For example, the central computer system 500 may be configured to provide or perform flash upgrades of the software run by the computer device 400. In the alternative, such software and/or data may also accessed by the computer device 400 at a specific site and then distributed to the measuring device 100 and/or locating device 300, if necessary.

According to further advantageous aspects of the present invention, the computer device 400 may be configured to communicate the collected data with a third party computer device 600 in addition to, or instead of, with the central computer system 500 associated with the contractor. For example, the third party computer device 600 may be associated with the owning entity and/or the particular state Department of Transportation. In such instances, the data collected from the measuring device 100/locating device 300 unit(s) by the computer device 400 may be associated with, for example, a time and date stamp, or an electronic identifier for the measuring device 100 (type and/or serial number), the operator thereof, the sample 200, the locating device 300, the computer device 400 receiving the data, the operator thereof, and/or the contractor, with each sample property/measuring device location measurement performed by the measuring device 100/locating device 300 unit and transmitted to the computer device 400. The data may be collected from the computer device 400, for example, in real time (as each data element is collected), at the conclusion of a planned series of measurements, at the end of a day, at the end of a job, or on an otherwise periodic basis, and then communicated with the third party computer device 600, preferably without allowing the raw data to be altered or otherwise manipulated by the operator of the measuring device 100, the locating device 300, or the computer device 400, or by the contractor. For example, the data could be written into a read-only file or the third party could assign a software security key to the data file on the computer device 400 so as to deter any tampering with the data written to the file. However, in some instances, the computer device 400 may be configured to provide a graphic depiction, such as a variety of graphs or graphics, of the data for display to the third party, wherein the graphical depiction would be provided in addition or in the alternative to the untouched raw data.

A system 10 as described herein provides distinct advantages over an integrated measuring device capable of addressing such data-related issues as previously described. For example, the manufacturer does not have to stock parts or pay for extra labor in the construction process as would be necessary for an integrated measuring device. Further, measuring device-specific software, I/O systems, and processors are not necessary. The manufacturer may further save costs by not having to develop specific hardware and/or software for the particular measuring device. In addition, older technology measuring devices 100 may be significantly and readily updated by configuring the computer device 400 to function as the user interface therefor, while a variety of programming languages and protocols may allow greater functionality and flexibility in the capabilities of the measuring devices 100 than previously possible. Also, the measuring device 100 and/or the locating device 300 may be readily configured or updated via a communication from the computer device 400 and/or the central, computer system 500 where, for example, the measuring device 100 and/or the locating device 300 may be remotely calibrated or have calibration parameters directed thereto. In other instances, for example, the measuring device 100 and/or the locating device 300 may be provided with a digital key from the central computing-device 500 to allow the measuring device 100 and/or the locating device 300 to be manually manipulated or manipulated via the computing device 400.

The customer (contractor) would also realise benefits from a system 10 as described. For example, the locating device 300 and/or the computer device 400 may be, in some instances, commercially available devices which may be readily configured for the functions as described herein. Accordingly, initial purchase costs and repair costs for the customer would be lower than specialty devices and the commercially available devices could be used for other purposes alternatively or in addition to the purposes as described herein. The customer could also readily alter existing software applications or independently develop software applications to custom tailor the system 10 to suit particular needs.

Many modifications and other embodiments of the invention set forth herein will come to mind to one skilled in the art to which this invention pertains having the benefit of the teachings presented in the foregoing descriptions and the associated drawings. For example, one skilled in the art will readily appreciate that a device comprising a measuring device, a locating device, and a computer device may be provided, as well as an apparatus comprising a measuring device and an associated locating device. More particularly, for instance, the measuring device and locating device may be configured to cooperate to send the relevant data directly to a central computer system or, in other instances, the measuring device may be configured to store the relevant data, which may then later be downloaded to a computer device for analysis. Further, one skilled in the art will also appreciate that the systems, devices, and methods described herein will readily lend themselves to one or more corresponding methods, computer devices, computer software program products, and/or the like within the spirit and scope of the present invention. In addition, the concepts, systems, apparatuses, and methods presented herein may be applicable in many different fields, besides the paving industry, in which it would be advantageous to combine the position indication of a GPS device with a particular measurement or event. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A measuring system comprising:
   a nuclear density gauge configured for being placed into contact with a paving-related material in order to take a measurement thereof, wherein the nuclear density gauge includes an interface for receiving operator input;
   a locating device operably engaged with the nuclear density gauge and configured to determine the location of the nuclear density gauge;
   a control system in communication with the locating device and the nuclear density gauge and configured to collect data by conducting a measurement in real time in which:
      the nuclear density gauge to takes a sample property measurement of the paving-related material; and
      the locating device determines the location of the nuclear density gauge,
      wherein the collected data includes the sample property measurement of the paving-related material and the determined location of the nuclear density gauge; and
   a computing device configured to receive the collected data that includes the sample property measurement of the paving-related material and the determined location of the nuclear density gauge, wherein the computing device is configured to write the collected data that includes the sample property measurement of the paving-related material and the determined location of the nuclear density gauge into a read-only file.

2. The system according to claim 1, wherein the nuclear density gauge includes a display for displaying instructions for being selected by a user.

3. The system according to claim 1, wherein conducting a measurement in real time comprises directing the locating device to determine the location of the nuclear density gauge as the nuclear density gauge takes the sample property measurement.

4. The system according to claim 3, wherein the determined location of the nuclear density gauge and the sample property measurement of the paving-related material are displayed on a display.

5. The system according to claim 1, wherein the paving-related material is a soil, asphalt, concrete or pavement surface.

6. The system according to claim 1, wherein the computing device is configured to associate a time and date stamp with the collected data that includes the sample property measurement of the paving-related material and the determined location of the nuclear density gauge.

7. The system according to claim 1, wherein the computing device is configured to associate an electronic identifier for the nuclear density gauge with the collected data that includes the sample property measurement of the paving-related material and the determined location of the nuclear density gauge.

8. The system according to claim 1, wherein the read-only file is assigned a software security key.

* * * * *